United States Patent [19] [11] 4,172,121
Calvin et al. [45] Oct. 23, 1979

[54] DENTIFRICE COMPOSITIONS CONTAINING FUMED SILICA WITH SORBED FLUORIDE

[75] Inventors: D. W. Calvin, Zachary; Marylu B. Gibbs, Baton Rouge, both of La.

[73] Assignee: The Dow Chemical Company, Midland, Mich.

[21] Appl. No.: 935,427

[22] Filed: Aug. 21, 1978

[51] Int. Cl.² ............................................. A61K 7/18
[52] U.S. Cl. ....................................................... 424/52
[58] Field of Search ................................... 424/49–58, 424/52

[56] References Cited

U.S. PATENT DOCUMENTS

| | | | |
|---|---|---|---|
| 3,862,307 | 1/1975 | Giulio | 423/335 X |
| 3,864,470 | 2/1975 | Watson | 424/49 |
| 3,934,000 | 1/1976 | Barth | 424/49 |
| 3,978,205 | 8/1976 | Newman et al. | 424/49 |
| 4,054,689 | 10/1977 | Calvin | 427/215 |

Primary Examiner—Shep K. Rose
Attorney, Agent, or Firm—James W. Ambrosius

[57] ABSTRACT

A dentifrice in a liquid vehicle containing fumed silica with fluoride sorbed thereon giving free fluoride ions in the composition for the therapeutic treatment of teeth.

3 Claims, No Drawings

DENTIFRICE COMPOSITIONS CONTAINING FUMED SILICA WITH SORBED FLUORIDE

BACKGROUND OF THE INVENTION

Dentifrice preparations typically contain a polishing or abrasive agent in combination with a gel or liquid vehicle and are intended for cleaning the teeth to aid in the prevention of tooth decay or dental caries. The dentifrice will often contain fluoride ions, commonly in the form of stannous fluoride or indium fluoride, which have been shown to be effective anti-caries agents. In recent years there has been increased interest in gel dentifrices, that is dentifrices which are visually substantially clear or translucent. Polishing or abrasive agents such as for example sodium carbonate or various insoluble magnesium salts render the dentifrice opaque and, therefore, are unsatisfactory for use in a gel dentifrice. Various types of silica have been found satisfactory for use as a polishing agent in the gel dentifrices because they have a refractive index which closely corresponds to that of the vehicle. In incorporating fluoride ions into a gel formulation containing silica, care must be exercised to assure the availability of sufficient anions to have the desired anti-caries effect. In addition, it is generally necessary to add the fluoride ion in a separate step from the silica material during manufacturing. U.S. Pat. No. 3,862,307 discloses a dentifrice composition containing an amorphous silica abrasive which has been pretreated with hydrofluoric acid. The composition is described as more compatable with therapeutic cations which are present in the formulation. However, this method of manufacture also requires a separate treatment step.

SUMMARY OF THE INVENTION

The present invention is directed to a dentifrice composition comprising from about 4 to about 7 percent by weight fumed silica with about 1 percent by weight to about 5 percent by weight of fluoride sorbed thereon in combination with a water soluble vehicle. Fumed silica refers to a fine particle, amorphous, pyrogenic silicon dioxide having a high surface area. Particle sizes generally range from about 70 to about 500 anstrom units. Fumed silica with fluoride sorbed thereon, sometimes referred to hydrophobic fumed silica, may be prepared according to the method described in U.S. Pat. No. 4,054,689. As used herein the term sorbed is meant to refer to fluoride values which are retained either physically or chemically by the $SiO_2$ regardless of whether the fluoride values are adsorbed, absorbed, or chemisorbed.

As contemplated by the present invention the fumed silica with fluoride sorbed thereon serves as a gelling or thickening agent in the dentifrice composition and, in addition, serves as a source of fluoride in the formulation. The fumed silica is compatable with other excipients commonly present in dentifrice compositions such as various surface active agents, additional abrasive particles, gelling agents, flavoring or sweeting materials, coloring agents, preservatives and the like.

The liquid vehicle in which the fumed silica and the other excipients are dispersed in generally an aqueous vehicle and may optionally contain other water soluble liquids such as for example gylcerin, propylene glycol, sorbitol solution, or alcohol and the like. If a gel dentifrice is intended the refractive index of the vehicle should closely approximate that of the fumed silica. In such applications, aqueous solutions of sorbitol and glycerin are generally satisfactory.

Additional thickners which are commonly employed in dentifrices include starch, tragacanth, algin, cellulose derivatives, polyvinyl pyrrolidone, and the like. Surface active agents may be anionic, cationic, nonionic, or ampholytic in nature.

The amount of free fluoride in the composition is generally between about 800 and 1200 parts per million. As used herein the phrase free fluoride refers to the amount of fluoride available for treatment of the teeth during use as opposed to bound fluoride which is reacted with or adsorbed by a component of the dentifrice and thus unavailable for treatment.

The present invention allows the fluoride to be incorporated into the dentifrice composition in a single mixing step. Determination of fluoride availability indicate the fluoride is available for therapeutic treatment of the teeth.

DETAILED DESCRIPTION OF THE INVENTION

The following examples will serve to further clarify the present invention, but are not to be construed as a limitation thereon.

EXAMPLE 1

A dentifrice was prepared using the following ingredients:

| Dentifrice Formulation | |
|---|---|
| Syloid ® 63 (W. R. Grace & Co.) | 18.6 grams |
| Fumed silica containing 2.7% fluoride | 4.1 |
| Polyethylene glycol (avg. m. w. 1540) | 5.2 |
| Sorbitol | 49.0 |
| Glycerin | 15.8 |
| Mixture containing 21% sodium lauryl sulfate and 79% glycerin | 7.2 |
| | 99.9 grams |

The above ingredients were blended by hand to incorporate the silicas as completely as possible. The composition was then mixed mechanically for 30 minutes.

EXAMPLE 2

The availability of fluoride ions was demonstrated by mixing 1 gram of the dentifrice composition prepared in Example 1 in 50 ml of distilled water. The mixture was stirred and then centrifuged about 10 minutes at 2000 rpm. The resulting supernatant was diluted 1:1 with a total ionic strength adjustment buffer (TISAB solution by Orion). The soluble fluorides were measured in the buffered solution using an Orion fluoride specific electrode. The results over a seventeen day period were as follows:

| Day After Dentifrice Prepared | Fluoride Ions (ppm) |
|---|---|
| 0 (initial measurement) | 1080 |
| 3 | 970 |
| 5 | 1050 |
| 17 | 1000 |

These data indicate the fluoride added to the formulation with the fumed silica is available as free fluoride in sufficient concentration to provide suitable therapeutic treatment. The amount of total fluoride calculated to be present in the above formulation is 1107 ppm. Therefore about 92.6% of the total fluoride present in the formulation was available as free fluoride.

We claim:

1. A dentifrice composition containing from about 4 to 7 percent by weight of fumed silica having from about 1 to about 5 percent by weight of fluoride sorbed thereon whereby free fluoride is released by the fumed silica in the composition in an amount of between about 800 and 1200 parts per million.

2. The composition of claim 1 wherein the liquid vehicle is water soluble.

3. A method for preparing a dentifrice in a liquid vehicle which comprises adding to the dentifrice composition from about 4 to about 7 percent by weight of fumed silica having from about 1 to about 5 percent by weight of fluoride sorbed thereon whereby free fluoride is released by the fumed silica in the composition in an amount of between about 800 and 1200 parts per million.

* * * * *